(12) United States Patent
Machida

(10) Patent No.: US 7,256,580 B2
(45) Date of Patent: Aug. 14, 2007

(54) MAGNETIC RESONANCE IMAGING APPARATUS AND MAGNETIC RESONANCE IMAGING METHOD

(75) Inventor: Yoshio Machida, Nasushiobara (JP)

(73) Assignees: Kabushiki Kaisha Toshiba, Tokyo (JP); Toshiba Medical Systems Corporation, Otawara-Shi, Tochigi-ken (JP)

( * ) Notice: Subject to any disclaimer, the term of this patent is extended or adjusted under 35 U.S.C. 154(b) by 155 days.

(21) Appl. No.: 11/226,324

(22) Filed: Sep. 15, 2005

(65) Prior Publication Data

US 2006/0064004 A1   Mar. 23, 2006

(30) Foreign Application Priority Data

Sep. 22, 2004   (JP)   ............... 2004-275687

(51) Int. Cl.
*G01V 3/00*   (2006.01)
(52) U.S. Cl. ...................... 324/318; 324/309
(58) Field of Classification Search ........ 324/300–322; 600/410–445
See application file for complete search history.

(56) References Cited

U.S. PATENT DOCUMENTS 5,566,279 A * 10/1996 Katayama ................... 345/419
5,631,560 A    5/1997 Machida
5,729,138 A    3/1998 Purdy et al.
5,891,032 A    4/1999 Harvey
6,998,841 B1 * 2/2006 Tamez-Pena et al. ....... 324/302

OTHER PUBLICATIONS

Blatter et al., "Cerebral MR Angiography with Multiple Overlapping This Slab Acquisition", Radiology, vol. 179, No. 3, Jun. 1991, pp. 805-811.
Liu et al., "Sliding Interleaved ky (SLINKY) Acquisition: A Novel 3D MRA Technique with Suppressed Slab Boundary Artifact", JMRI, vol. 8, No. 4, Jul./Aug. 1998, 903-911.

* cited by examiner

*Primary Examiner*—Brij Shrivastav
(74) *Attorney, Agent, or Firm*—Nixon & Vanderhye P.C.

(57) ABSTRACT

A magnetic resonance imaging apparatus comprising an imaging condition setting unit, a gradient coil, a radio frequency coil, a data acquisition unit, an image reconstructing unit and an image data generating unit. The imaging condition setting unit sets a first imaging condition and a second imaging condition at least. The data acquisition unit acquires first magnetic resonance signal data corresponding to the first imaging condition and second magnetic resonance signal data corresponding to the second imaging condition. The image reconstructing unit reconstructs first three dimensional image data in accordance with the first magnetic resonance signal data and second three dimensional image data in accordance with the second magnetic resonance signal data. The image data generating unit combines the first three dimensional image data and the second three dimensional image data to generate third three dimensional image data.

25 Claims, 9 Drawing Sheets

SCAN FOR s1 (WITH FAT SATURATION)
↓
SCAN FOR s2 (WITH FAT SATUVATION)
↓
⋮
↓
SCAN FOR si-1 (WITH FAT SATURATION)
↓
SCAN FOR si (WITH FAT SATURATION)
↓
SCAN FOR si (WITHOUT FAT SATURATION)
↓
SCAN FOR si+1 (WITH FAT SATURATION)
↓
⋮
↓
SCAN FOR sn-1 (WITH FAT SATURATION)
↓
SCAN FOR sn (WITH FAT SATURATION)

MAGNETIC RESONANCE IMAGING APPARATUS AND MAGNETIC RESONANCE IMAGING METHOD

BACKGROUND OF THE INVENTION

1. Field of the Invention

The present invention relates to a magnetic resonance imaging apparatus and a magnetic resonance imaging method which excite nuclear spin of an object magnetically with a RF signal having the Larmor frequency and reconstruct an image based on a magnetic resonance signal generated due to the excitation, and more particularly, to a magnetic resonance imaging apparatus and a magnetic resonance imaging method, which reconstruct an image with suppression or excitation of a magnetic resonance signal from a specific part, such as fat-saturation.

2. Description of the Related Art

Magnetic Resonance Imaging (MRI) is an imaging method which excite nuclear spin of an object set in a static magnetic field with a radio frequency (RF) signal having the Larmor frequency magnetically and reconstruct an image based on a magnetic resonance (MR) signal generated due to the excitation.

In the field of magnetic resonance imaging, MRA (magnetic resonance angiography) is known as a method for obtaining an image of the blood flow at a desired portion, such as the head, lung field, or stomach. The MRA includes enhanced MRA and un-enhanced MRA. The enhanced MRA is an imaging method with a contrast medium injected to an object. The un-enhanced MRA is an imaging method without a contrast medium. In any MRA, importantly, in order to obtain the image of the blood flow, an MR signal from a fat is suppressed and an MR signal from water, serving as a component of the blood flow, is excited, thereby sufficiently obtaining the contrast between a blood flow region and a parenchymal region other than the blood flow region.

Conventionally, a fat-water separation method is used. According to the fat-water separation method, an MR signal (fat signal) from the fat is suppressed by using the difference (chemical shift) in resonant frequencies between protons of fat and water. The fat-water separation method includes a pre-pulse method and a water excitation method. The pre-pulse method has been put into practical use. According to the pre-pulse method, a fat saturation pulse for suppressing a fat signal is applied to the object, as a pre-pulse prior to imaging a blood flow. This pre-pulse selectively excites only the fat depending on frequencies so that protons of the fat are saturated. Subsequently, an imaging of blood flow starts. According to the water excitation method, a water excitation pulse is applied, as an excitation pulse. The improvement in this water excitation pulse enables the excitation of only the MR signal (water signal) from the water without generating the fat signal.

Further, according to the fat-water separation method using the pre-pulse method, in order to prevent a trouble of the reduction in water signal due to the small difference in resonant frequencies between protons of a fat and water, an improvement in a frequency band of a fat saturation pulse to suppress the reduction in a water signal is suggested (see, for example, JP-A-2002-306447).

When a frequency shifted from the resonant frequency of protons of water by 500 Hz is selectively excited by an RF pulse, an MR signal level from protons of a high polymer, serving as a fat component, and an MR signal level from protons of water are reduced respectively. Advantageously, an image with the contrast depending on the rate of high polymers is obtained. In this case, an MR signal level at the fat region is excessively reduced, as compared with an MR signal level at the blood flow region.

In order to obtain the above-mentioned MT (magnetization transfer) advantages, a technology for applying an RF pulse, so-called MTC (magnetization transfer contrast) pulse, as a pre-pulse to the object prior to imaging, is proposed. This technology is applied to an MRA with the extraction of a little blood vessel (see, for example, JP-A-H06-319715).

Further, based on three dimensional (3D) image data obtained with various improving technologies of contrast for applying a fat saturation pulse, a water excitation pulse, and an MTC pulse, imaging processing such as MIP (maximum intensity projection) processing generates three dimensional image data for diagnosis, such as an MIP image.

A fat saturation or a water excitation under the conventional MRA uses the difference (chemical shift) in resonant frequencies between protons of a fat and water. Therefore, when a region as an imaging target includes an uneven magnetic field, there is a problem that a fat signal cannot be properly suppressed or a water signal cannot be properly excited. In particular, in the case of MRA of the head of the object, the region near a curve portion of a blood vessel passing through the bone portion ranging from a carotid pyramidal portion to a syphone partly includes uneven magnetic field. Therefore, the fat signal is not preferably suppressed and the water signal is not preferably excited. The MR signal from the water component is lost and an MRA image with the lost blood flow region may be generated.

Currently, the improvement in sequence waveform, serving as an imaging condition, cannot solve the problem regarding as the loss of the blood flow region on the MRA image obtained in a region having an uneven magnetic field.

Then, when the uneven magnetic field is not ignored and a fat signal cannot be preferably suppressed or a water signal cannot be preferably excited, the image is obtained without the fat saturation or the water excitation. Then, the image data as an imaging result is subjected to imaging processing, such as region processing, thereby generating image data suitable for diagnosis.

For example, in the case of the MRA of the head for generating a blood flow image of the head, a fat region near a scalp does not enable the extraction of blood vessel. Therefore, the fat region needs to be removed from the image data. Then, for the image data obtained by the imaging without the fat saturation of head, an inner region of the scalp is set as a region of interest (ROI), thereby removing the peripheral fat region including the scalp from the image data. Then, only the image data at the inner region of the scalp is subjected to specific MIP processing, such as Partial-MIP processing, thereby generating the image data suitable to the diagnosis.

As a consequence, a troublesome operation including the setting of an ROI and the removal of image data at the fat region is needed. In particular, in Whole Brain MRA, the operation including the setting of an ROI and the removal of image data at the fat region is more complicated and further impossible.

That is, the conventional technologies of the fat saturation and water excitation cannot be applied to a portion, such as a curve portion with an uneven magnetic field particularly, and need specific image processing, such as Partial MIP for generating an image data for diagnosis. In other words, in the case of obtaining an MRA image at a portion such as a curve portion, the conventional technologies of the fat saturation and water excitation have a problem that it is not possible to obtain the original merit of the conventional technologies of the fat saturation and water excitation, that is, a merit for obtaining an MRA image with a small loss of the blood vessel region at a wide area without specific imaging processing.

SUMMARY OF THE INVENTION

The present invention has been made in light of the conventional situations, and it is an object of the present invention to provide a magnetic resonance imaging apparatus and a magnetic resonance imaging method which make it possible to obtain a MRA image having few deficits of a blood vessel without performing a special MIP processing, such as Partial MIP processing, due to a contrast improvement technology based on an imaging condition, such as fat-saturation and water excitation, even if it is the case where a MRA image in part which is easy to become uneven a magnetic field, such as a flexion part, is to be obtained.

The present invention provides a magnetic resonance imaging apparatus comprising: an imaging condition setting unit configured to set a first imaging condition and a second imaging condition at least; a gradient coil configured to impress gradient magnetic fields to an object in a static magnetic field in accordance with the first imaging condition and the second imaging condition; a radio frequency coil configured to transmit radio frequency signals to the object in accordance with the first imaging condition and the second imaging condition; a data acquisition unit configured to acquire first magnetic resonance signal data corresponding to the first imaging condition and second magnetic resonance signal data corresponding to the second imaging condition from the object; an image reconstructing unit configured to reconstruct first three dimensional image data regarding the object in accordance with the first magnetic resonance signal data and second three dimensional image data regarding the object in accordance with the second magnetic resonance signal data; and an image data generating unit configured to combine the first three dimensional image data and the second three dimensional image data to generate third three dimensional image data, in an aspect to achieve the object.

The present invention also provides a magnetic resonance imaging apparatus comprising: means for setting a first imaging condition and a second imaging condition at least; means for impressing gradient magnetic fields to an object in a static magnetic field in accordance with the first imaging condition and the second imaging condition; means for transmitting radio frequency signals to the object in accordance with the first imaging condition and the second imaging condition; means for acquiring first magnetic resonance signal data corresponding to the first imaging condition and second magnetic resonance signal data corresponding to the second imaging condition from the object; means for reconstructing first three dimensional image data regarding the object in accordance with the first magnetic resonance signal data and second three dimensional image data regarding the object in accordance with the second magnetic resonance signal data; and means for combining the first three dimensional image data and the second three dimensional image data to generate third three dimensional image data, in an aspect to achieve the object.

The present invention also provides a magnetic resonance imaging method comprising steps of: setting a first imaging condition and a second imaging condition at least; impressing gradient magnetic fields to an object in a static magnetic field in accordance with the first imaging condition and the second imaging condition; transmitting radio frequency signals to the object in accordance with the first imaging condition and the second imaging condition; acquiring first magnetic resonance signal data corresponding to the first imaging condition and second magnetic resonance signal data corresponding to the second imaging condition from the object; reconstructing first three dimensional image data regarding the object in accordance with the first magnetic resonance signal data and second three dimensional image data regarding the object in accordance with the second magnetic resonance signal data; and combining the first three dimensional image data and the second three dimensional image data to generate third three dimensional image data, in an aspect to achieve the object.

The magnetic resonance imaging apparatus and the magnetic resonance imaging method as described above make it possible to obtain a MRA image having few deficits of a blood vessel without performing a special MIP processing, such as Partial MIP processing, due to a contrast improvement technology based on an imaging condition, such as fat-saturation and water excitation, even if it is the case where a MRA image in part which is easy to become uneven a magnetic field, such as a flexion part, is to be obtained.

DESCRIPTION OF THE PREFERRED EMBODIMENTS

A magnetic resonance imaging apparatus and a magnetic resonance imaging method according to embodiments of the present invention will be described with reference to the accompanying drawings.

Figure 1:
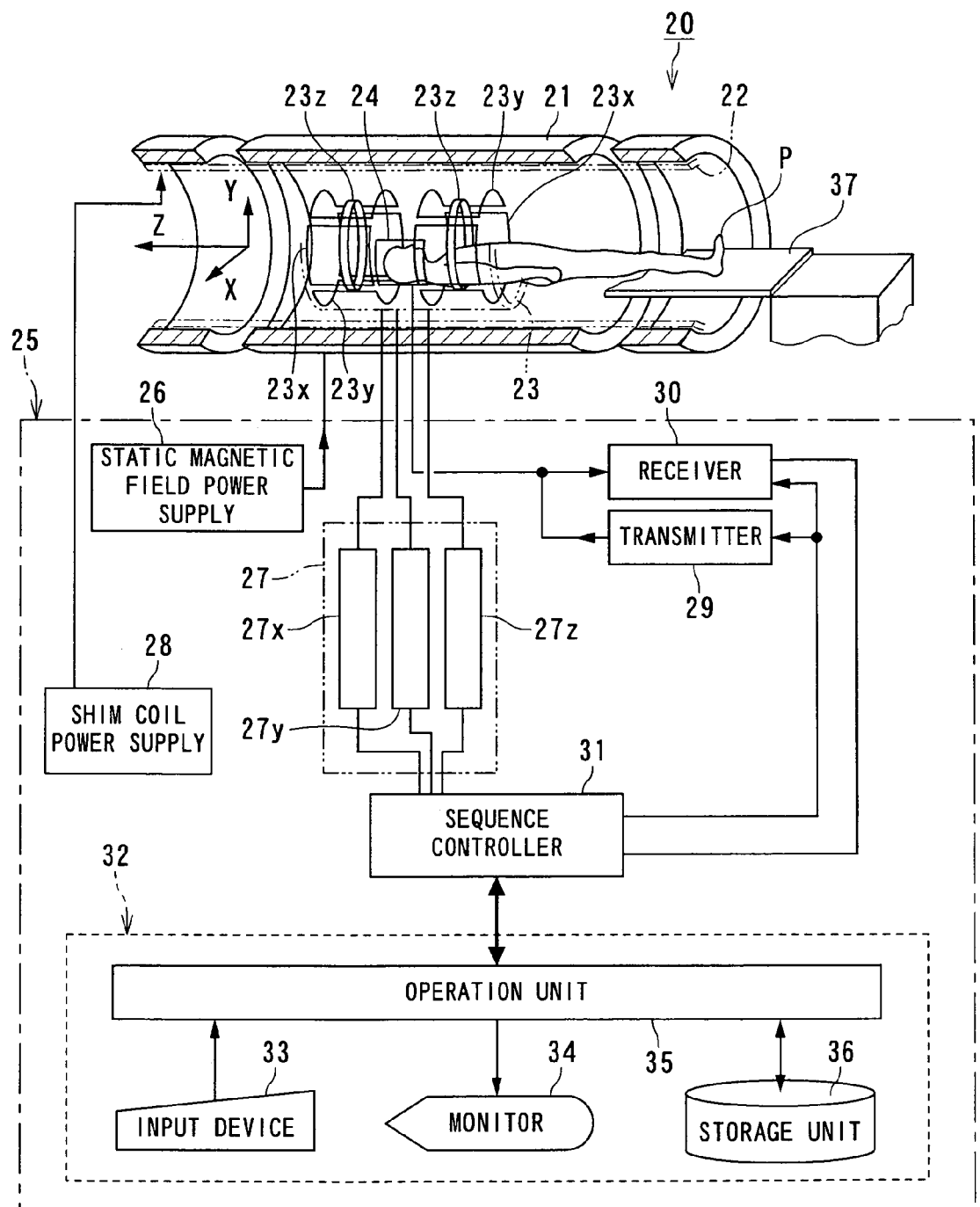
FIG. 1 is a block diagram showing a magnetic resonance imaging apparatus according to a first embodiment of the present invention.

FIG. 1 is a block diagram showing a magnetic resonance imaging apparatus according to a first embodiment of the present invention.

A magnetic resonance imaging apparatus 20 includes a static field magnet 21 for generating a static magnetic field, a shim coil 22 arranged inside the static field magnet 21 which is cylinder-shaped, a gradient coil unit 23 and a RF coil 24. The static field magnet 21, the shim coil 22, the gradient coil unit 23 and the RF coil 24 are built in a gantry (not shown).

The magnetic resonance imaging apparatus 20 also includes a control system 25. The control system 25 includes a static magnetic field power supply 26, a gradient power supply 27, a shim coil power supply 28, a transmitter 29, a receiver 30, a sequence controller 31 and a computer 32. The gradient power supply 27 of the control system 25 includes an X-axis gradient power supply 27x, a Y-axis gradient power supply 27y and a Z-axis gradient power supply 27z. The computer 32 includes an input device 33, a monitor 34, a operation unit 35 and a storage unit 36.

The static field magnet 21 communicates with the static magnetic field power supply 26. The static magnetic field power supply 26 supplies electric current to the static field magnet 21 to get the function to generate a static magnetic field in a imaging region. The static field magnet 21 includes a superconductivity coil in many cases. The static field magnet 21 gets current from the static magnetic field power supply 26 which communicates with the static field magnet 21 at excitation. However, once excitation has been made, the static field magnet 21 is usually isolated from the static magnetic field power supply 26. The static field magnet 21 may include a permanent magnet which makes the static magnetic field power supply 26 unnecessary.

The static field magnet 21 has the cylinder-shaped shim coil 22 coaxially inside itself. The shim coil 22 communicates with the shim coil power supply 28. The shim coil power supply 28 supplies current to the shim coil 22 so that the static magnetic field becomes uniform.

The gradient coil unit 23 includes an X-axis gradient coil unit 23x, a Y-axis gradient coil unit 23y and a Z-axis gradient coil unit 23z. Each of the X-axis gradient coil unit 23x, the Y-axis gradient coil unit 23y and the Z-axis gradient coil unit 23z which is cylinder-shaped is arranged inside the static field magnet 21. The gradient coil unit 23 has also a bed 37 in the area formed inside it which is an imaging area. The bed 37 supports an object P. Around the bed 37 or the object P, the RF coil 24 may be arranged instead of being built in the gantry.

The gradient coil unit 23 communicates with the gradient power supply 27. The X-axis gradient coil unit 23x, the Y-axis gradient coil unit 23y and the Z-axis gradient coil unit 23z of the gradient coil unit 23 communicate with the X-axis gradient power supply 27x, the Y-axis gradient power supply 27y and the Z-axis gradient power supply 27z of the gradient power supply 27 respectively.

The X-axis gradient power supply 27x, the Y-axis gradient power supply 27y and the Z-axis gradient power supply 27z supply currents to the X-axis gradient coil unit 23x, the Y-axis gradient coil unit 23y and the Z-axis gradient coil unit 23z respectively so as to generate gradient magnetic fields Gx, Gy and Gz in the X, Y and Z directions in the imaging area.

The RF coil 24 communicates with the transmitter 29 and the receiver 30. The RF coil 24 has a function to transmit a RF signal given from the transmitter 29 to the object P and receive a MR signal generated due to an nuclear spin inside the object P which is excited by the RF signal to give to the receiver 30.

The sequence controller 31 of the control system 25 communicates with the gradient power supply 27, the transmitter 29 and the receiver 30. The sequence controller 31 has a function to storage sequence information describing control information needed in order to make the gradient power supply 27, the transmitter 29 and the receiver 30 drive and generate gradient magnetic fields Gx, Gy and Gz in the X, Y and Z directions and a RF signal by driving the gradient power supply 27, the transmitter 29 and the receiver 30 according to a predetermined sequence stored. The control information above-described includes motion control information, such as intensity, impression period and impression timing of the pulse electric current which should be impressed to the gradient power supply 27

The sequence controller 31 is also configured to give raw data to the computer 32. The raw data is complex number data obtained through the detection of a MR signal and A/D conversion to the MR signal detected in the receiver 30.

The transmitter 29 has a function to give a RF signal to the RF coil 24 in accordance with control information provided from the sequence controller 31. The receiver 30 has a function to generate raw data which is digitized complex number data by detecting a MR signal given from the RF coil 24 and performing predetermined signal processing and A/D converting to the MR signal detected. The receiver 30 also has a function to give the generated raw data to the sequence controller 31.

In the example of this embodiment, the elements, i.e., the static field magnet 21 the shim coil 22 the gradient coil unit 23, the RF coil 24 and the control system 25, give a function as a raw data acquisition unit to the magnetic resonance imaging apparatus 20, the raw data acquisition unit impressing a gradient magnetic field and transmitting a RF signal to the object P in a static magnetic field in accordance with imaging condition determined as a sequence and generating raw data by receiving a MR signal produced with a nuclear magnetic resonance of a nucleus due to a RF signal in the object P and digitizing the received MR signal.

The computer 32 gets various functions by the operation unit 35 executing some programs stored in the storage unit 36 of the computer 32. The computer 32 may include some specific circuits instead of using some of the programs.

Figure 2:
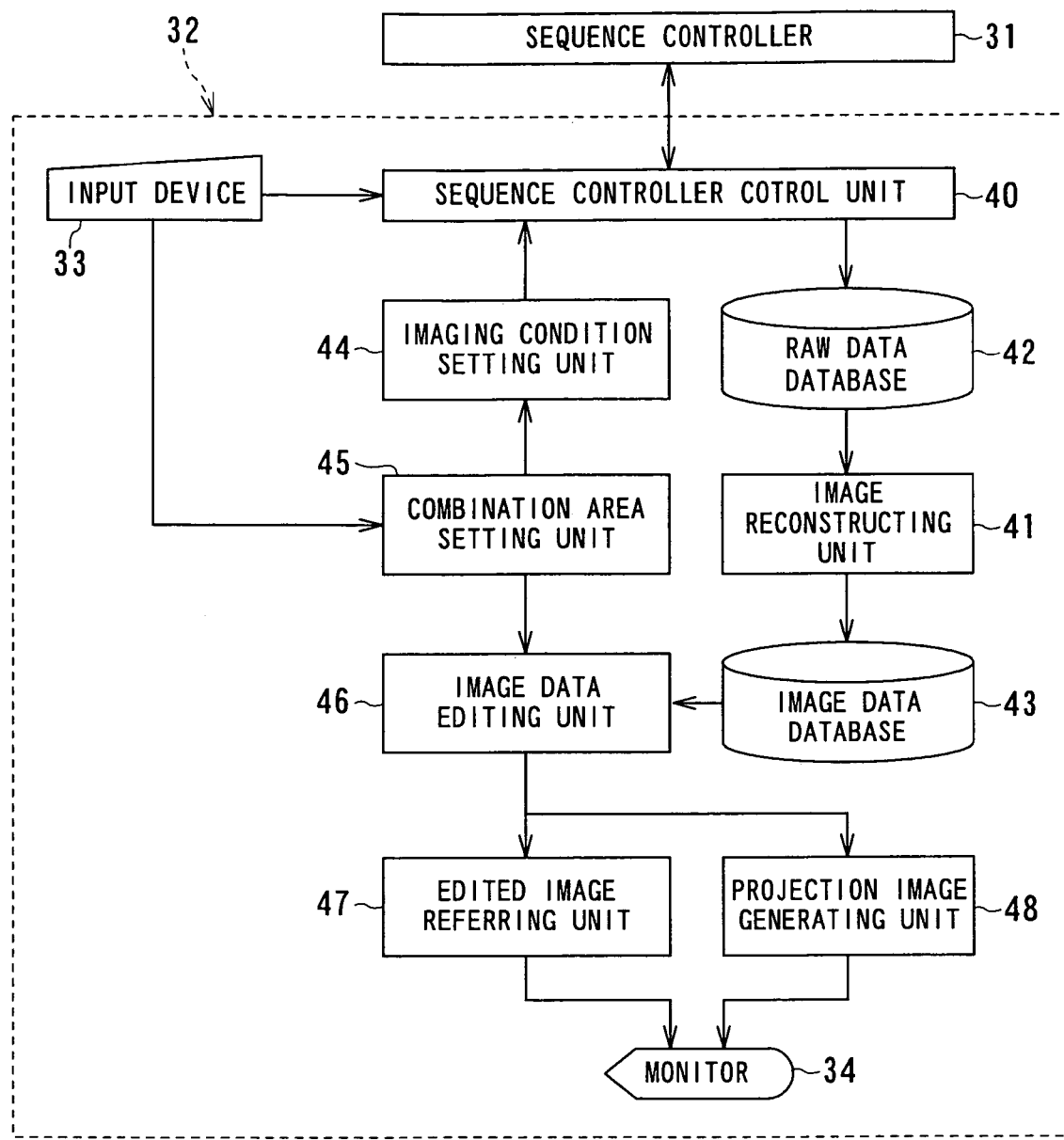
FIG. 2 is a functional block diagram of the computer in the magnetic resonance imaging apparatus shown in FIG. 1.

FIG. 2 is a functional block diagram of the computer 32 in the magnetic resonance imaging apparatus 20 shown in FIG. 1.

The computer 32 functions as a sequence controller control unit 40, an image reconstructing unit 41, a raw data database 42, an image data database 43, an imaging condition setting unit 44, a combination area setting unit 45, an image data editing unit 46, an edited image referring unit 47 and a projection image generating unit 48.

The sequence controller control unit 40 has a function for controlling the driving of the sequence controller 31 by giving predetermined sequence information to the sequence controller 31 based on information from the input device 33 or another element. In particular, the sequence controller control unit 40 enables the scanning operation with switching the existence of fat-water separation by giving a sequence for fat-water separation in addition to a normal sequence without the fat-water separation to the sequence controller 31 at an arbitrary timing.

Incidentally, the fat-water separation method includes a pre-pulse method and a water excitation method. According to the pre-pulse method, prior to imaging the blood flow, a fat saturation pulse for saturating a fat signal is applied to an object, as a pre-pulse, only the fat is selectively excited depending on the frequency, protons of the fat are saturated, and the imaging of blood flow thereafter starts. According to the water excitation method, a water excitation pulse is applied, as an excitation pulse, and only an MR signal (water signal) from water is excited without generating a fat signal. Any of the above-mentioned fat-water separation methods may be used.

Further, the sequence controller control unit 40 has a function for receiving raw data from the sequence controller 31 and arranging the raw data to k space (Fourier space) formed in the raw data database 42.

Therefore, the raw data database 42 stores the raw data generated by the receiver 30, and the raw data is arranged to the k space formed in the raw data database 42.

The image reconstructing unit 41 has a function for capturing the raw data from the raw data database 42, performing predetermined image reconstruction processing, such as three dimensional (3D) Fourier transform processing, reconstructing three dimensional image data of the object P, and writing the image data to the image data database 43. Incidentally, intermediate data, such as two dimensional (2D) image data, may be temporarily generated by processing, such as two dimensional Fourier transform processing, and thereafter the three dimensional image data may be reconstructed.

Therefore, the image data database 43 stores the three dimensional image data of the object P. In particular, in the case of executing the scanning operation with switching the existence of the fat-water separation (including the fat saturation and the water excitation), the image data database 43 stores the three dimensional image data obtained with the fat-water separation and the three dimensional image data without the fat-water separation.

The imaging condition setting unit 44 has a function for generating a sequence for scanning operation with switching the existence of the fat-water separation, and giving the generated sequence to the sequence controller control unit 40, that is, function for setting an imaging condition. That is, the imaging condition setting unit 44 generates the whole sequence by combining a sequence for executing the scanning operation without the fat-water separation to the sequence for executing the scanning operation with the fat-water separation. In this case, preferably, at an imaging region common to the scanning operation with the fat-water separation and to the scanning operation without the fat-water separation the sequence is formed so that an imaging interval is shorter.

Incidentally, the sequence for executing the scanning operation with the fat-water separation and the sequence for executing the sequence for the scanning operation without the fat-water separation can be independently generated and each of the generated sequences may be individually given to the sequence controller control unit 40.

The setting of an imaging condition for deciding whether scanning is executed with the fat-water separation or without the fat-water separation refers to a replacement area of the three dimensional image data received from the combination area setting unit 45, which will be described later.

The image data editing unit 46 has a function for additionally generating three dimensional image data by combining the three dimensional image data with the fat-water separation and the three dimensional image data without the fat-water separation, and a function for giving the generated three dimensional image data to the projection image generating unit 48 and the edited image referring unit 47. The combining method of the three dimensional image data includes a method for partly replacing the three dimensional image data with the fat-water separation with the three dimensional image data without the fat-water separation, a method contrary to the above-mentioned one and a method for simply adding the three dimensional image data each other.

Further, the image data editing unit 46 has a function for weighting the three dimensional image data with the fat-water separation and the three dimensional image data without the fat-water separation if necessary so as to smooth the additionally-generated three dimensional image.

The combination area setting unit 45 has a function setting a combination area on combining the three dimensional image data with the fat-water separation and the three dimensional image data without the fat-water separation by the image data editing unit 46. In the case of partly replacing the three dimensional image data with the fat-water separation to the three dimensional image data without the fat-water separation, the replacement area is set based on area designating information, such as designating information of the replacement area, received from the input device 33.

Further, the combination area setting unit 45 has a function for giving the set combination area, such as the replacement area, to the image data editing unit 46 and the imaging condition setting unit 44.

Incidentally, the combination area including the replacement area can be automatically performed by various processing, such as threshold processing of the three dimensional image data, or by reference to another image data. Further, in order to designate the combination area, arbitrary image data such as SVR (Shaded volume rendering) image data or MIP image data can be generated, as reference image data, and can be sent to a monitor 34, thereby easily grasping the entire three dimensional image data spatially.

The edited image referring unit 47 has a function for performing required imaging processing to the three dimensional image data received from the image data editing unit 46 so as to generate image data, giving the generated image data to the monitor 34, and displaying the image for reference. The image for reference can be an arbitrary image including an MIP image. Then, the edited image referring unit 47 performs processing of the three dimensional image data received from the image data editing unit 46 in accordance with the format of image for reference.

The projection image generating unit 48 has a function for generating MIP image data by performing the MIP processing of the three dimensional image data received from the image data editing unit 46, and a function for giving the generated MIP image data to the monitor 34 so as to display the MIP image.

With these functions of the computer 32, the magnetic resonance imaging apparatus 20 has a function for combining image data obtained by executing the scanning operation with the fat-water separation and the scanning operation without the fat-water separation so as to generate additionally image data. Further, the functions of the magnetic resonance imaging apparatus 20 executes the scanning operation without the fat-water separation of the portion having the uneven magnetic field where a proper fat-water separation doesn't work, and executes the scanning operation with the fat-water separation of the portion where a proper fat-water separation works, on imaging of the MRA image of the object P.

The three-dimensional image data obtained respectively are combined each other, thereby obtaining the MRA image with preferable contrast.

Next, the operation of a magnetic resonance imaging apparatus 20 will be described.

Figure 3:
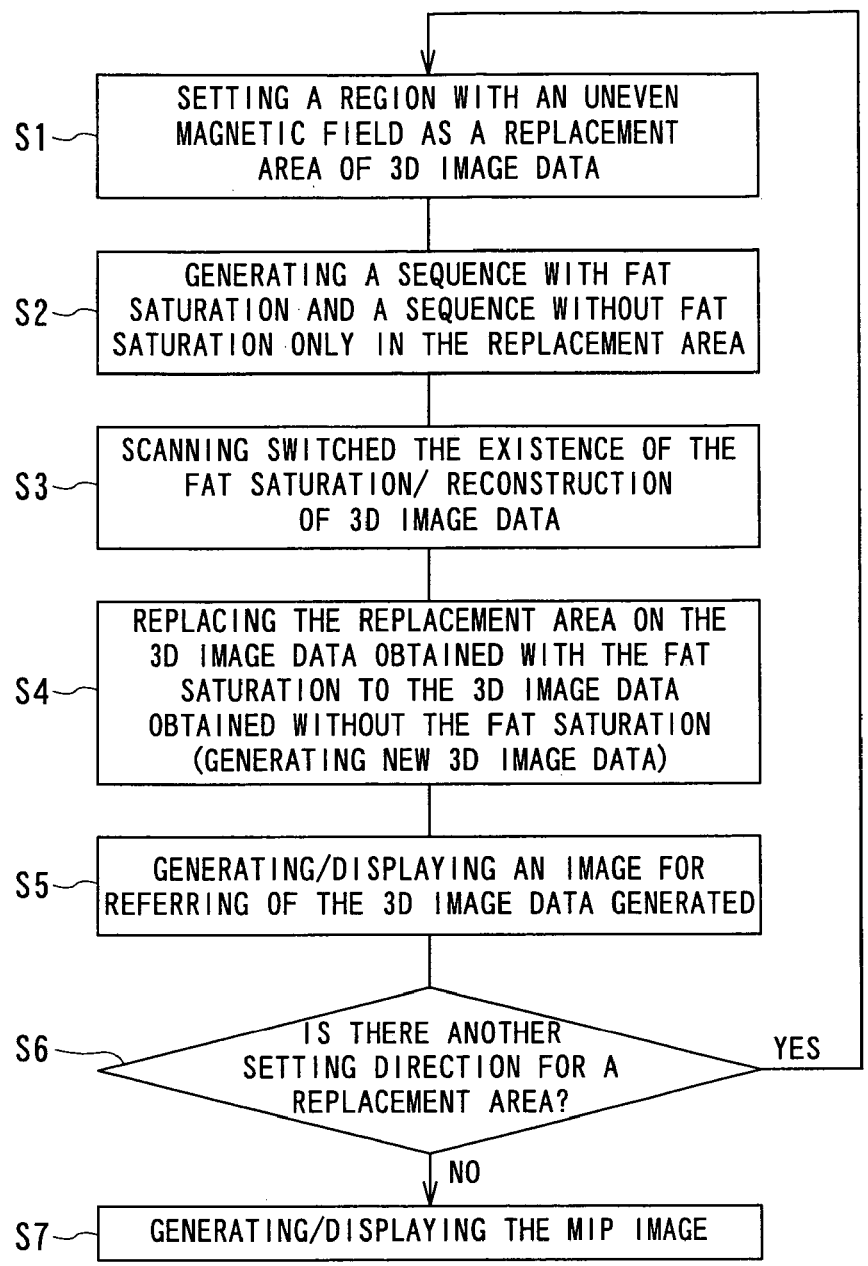
FIG. 3 is a flowchart showing an example of flow for imaging a MRA image according to the head of the object with the magnetic resonance imaging apparatus shown in FIG. 1.

FIG. 3 is a flowchart showing an example of flow for imaging a MRA image according to the head of the object P with the magnetic resonance imaging apparatus 20 shown in FIG. 1. The symbols including S with a number in FIG. 3 indicate each step of the flowchart.

In step S1, the operation of the input device 33 designates, as a replacement area of the three dimensional image data, a portion estimated as one having an uneven magnetic field within an imaging range of the object P, e.g., a curve portion of the blood vessel passing through a bone portion ranging from a carotid pyramidal portion to a syphone. That is, the fat is saturated at the portion with the uneven magnetic field and then the advantages of fat-water separation are not preferably obtained. There is a danger that the MR signal from the water component is lost and the MRA image having the lost blood flow region is generated.

Therefore, preferably, at the portion with the uneven magnetic field, e.g., the curve portion, the scanning operation is executed without the fat-water separation and the three dimensional image data is reconstructed. Preferably, at a portion with an even magnetic field, the fat-water separation is executed and the three dimensional image data is reconstructed.

Then, the magnetic resonance imaging apparatus 20 switches the existence of the fat-water separation for each of the imaging portions, that is, each of imaging slices, then, the scanning operation is executed. Therefore, the three dimensional image data reconstructed with the fat-water separation is partly replaced with the three dimensional image data reconstructed without the fat-water separation. In this case, the replacement area is designated in advance.

Figure 4:
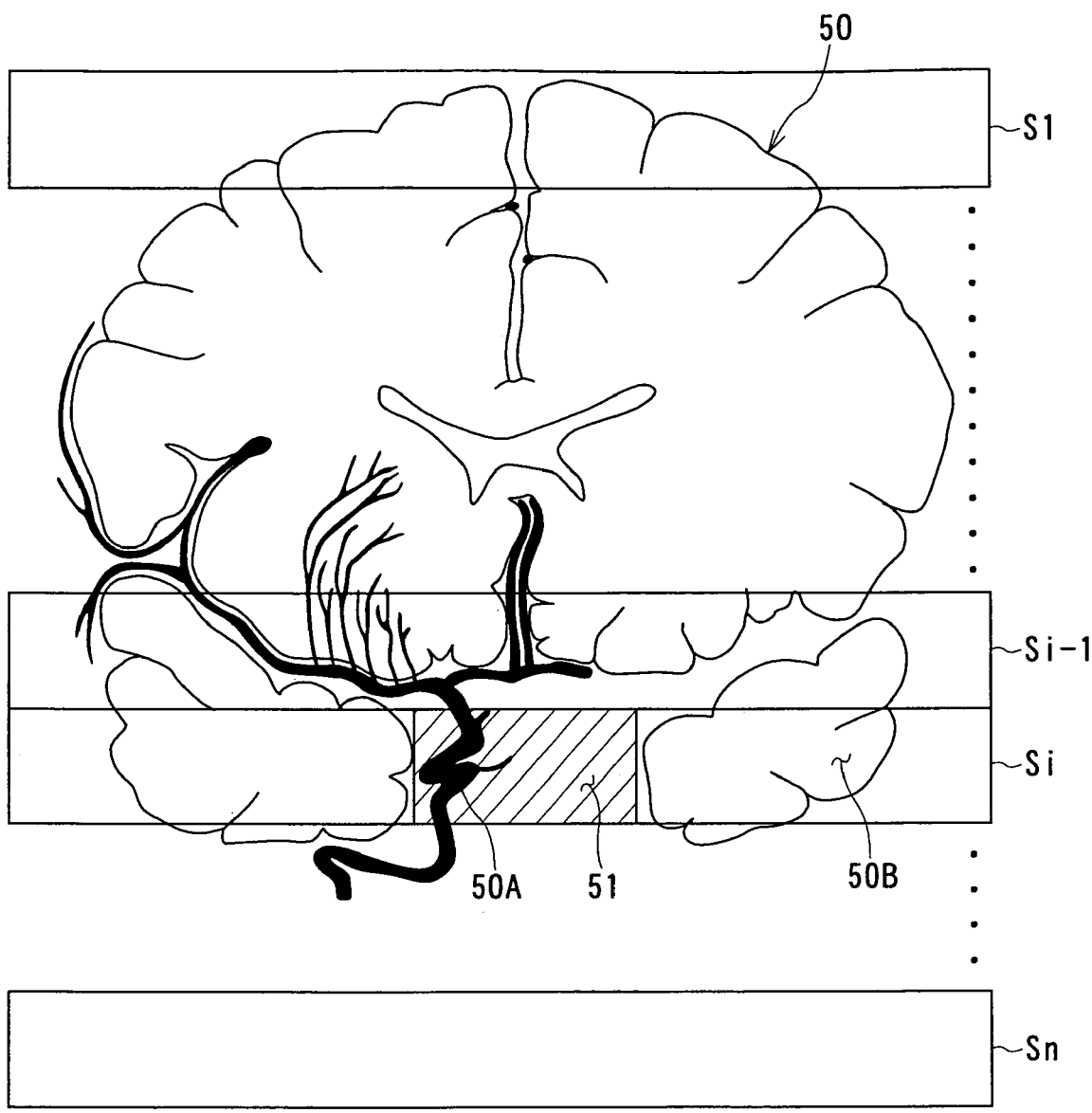
FIG. 4 is a diagram showing the position of the carotid syphone of the head determined as an example of a replacement area on three dimensional image data in the magnetic resonance imaging apparatus shown in FIG. 1.

FIG. 4 is a diagram showing the position of the carotid syphone of the head determined as an example of a replacement area on three dimensional image data in the magnetic resonance imaging apparatus 20 shown in FIG. 1.

Referring to FIG. 4, near a carotid syphone 50A of a head 50, the magnetic field is uneven. If the fat-water separation is performed, there is a danger that the effect of fat-water separation is not preferably obtained and the MR signal from the water component is lost. Therefore, preferably, near the carotid syphone 50A of the head 50, the scanning operation is executed without the fat-water separation and the three dimensional image data is reconstructed.

However, the MR signal from a portion 50B other than the carotid syphone 50A of the head 50, particularly, the fat region near the scalp is an obstacle upon extracting the blood vessel. Preferably, the fat-water separation is performed and the three dimensional image data is reconstructed.

The combination area setting unit 45 generates the three dimensional image data serving as image data for reference, such as MIP image data imaged in advance for reference or tomographic image data of the head 50. Then, the combination area setting unit 45 gives the generated image data for reference to the monitor 34. Therefore, a reference image for setting the combined region as shown in FIG. 4 is displayed on the monitor 34 for example.

A user refers to the reference image, such as the MIP image of the head, and can designate a curve portion 51, e.g., near the carotid syphone 50A, as the replacement area for the three dimensional image data, by the operation of the input device 33. The input device 33 gives the replacement area of the three dimensional image data to the combination area setting unit 45, and the replacement area of the three dimensional image data is set. The combination area setting unit 45 gives the replacement area of the three dimensional image data to the image data editing unit 46 and the imaging condition setting unit 44.

In step S2, the imaging condition setting unit 44 refers to the replacement area of the three dimensional image data received from the combination area setting unit 45, and generates a sequence obtained by combining the sequence for executing the scanning operation of the entire head of the object P with the fat-water separation and the sequence for executing the scanning operation of only the replacement area of the head without the fat-water separation.

Incidentally, with respect to each imaging condition which does not contribute to the fat-water separation, the imaging condition of the scanning operation with the fat-water separation may be the same as that of the scanning operation without the fat-water separation or may be different therefrom. Each of the imaging conditions which do not contribute to the fat-water separation is properly set depending on the diagnostic target and an imaging method.

Figure 5:
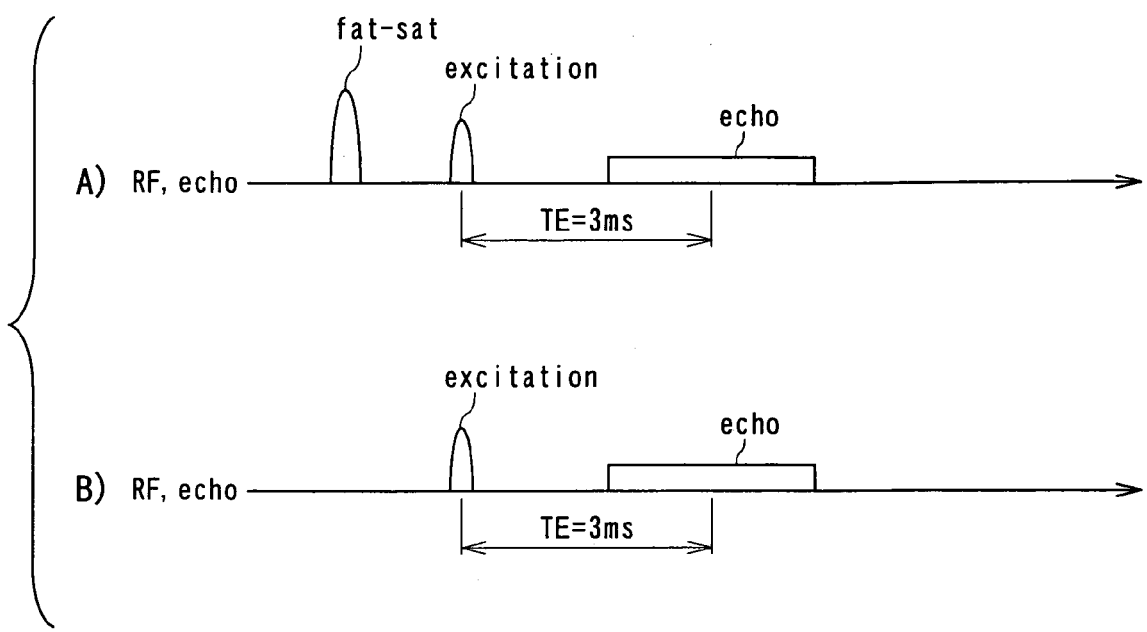
FIG. 5 is a diagram showing an example of a sequence used in a case where a scan is performed with switching the existence of the fat-water separation with a pre-pulse method while fundamental imaging conditions are to be identity in the magnetic resonance imaging apparatus shown in FIG. 1.

FIG. 5 is a diagram showing an example of a sequence used in a case where a scan is performed with switching the existence of the fat-water separation with a pre-pulse method while fundamental imaging conditions are to be identity in the magnetic resonance imaging apparatus 20 shown in FIG. 1.

Referring to FIG. 5, a sequence for acquiring the MR signal with the fat saturation under the pre-pulse method is generated for imaging the slices overall the head of the object P. Another sequence for acquiring the MR signal without the fat saturation is generated for imaging the slices including the replacement area of the three dimensional image data.

The sequence with the fat saturation is configured to apply a fat saturation pulse in prior to an excitation pulse as shown in A) of FIG. 5. An echo time (TE) until acquiring the MR signal (echo) is equal to 3 ms for example. With respect to the slice, referring to FIG. 4, a number n of slices (s1, s2, . . . , sn) in the axial direction is plural and each of the slices is properly set with an arbitrary thickness. Therefore, a slice si partly includes the curve portion 51, e.g., near the carotid syphone 50A. Then, a gradient magnetic pulse in a slice (SL) direction is set so that all slices of the head are to be scanning targets.

Referring to B) of FIG. 5, the sequence without the fat saturation is different from the sequence shown A) of FIG. 5, only in the imaging condition that the fat saturation pulse is deleted. Then, the gradient magnetic pulse in the slice direction is set so that the slice, si including the curve portion 51, e.g., near the carotid syphone 50A, is to be a scanning target. Further, parameters of general imaging conditions other than a sequence, such as a field of view (FOV) are set to the same irrespective of the case with the fat saturation and the case without the fat saturation.

That is, FIG. 5 shows an example that the imaging conditions other than the fat saturation pulse contributing to the fat saturation are set to the same, irrespective of the existence of the fat saturation. As mentioned above, the imaging conditions are the same, thereby obtaining the image data under the single imaging condition in the case of combining the three dimensional image data later. Then, the MRA image under the equivalent imaging condition can be obtained.

Incidentally, in case with the fat-water separation under the water excitation method, imaging conditions other than those contributing to the water excitation may be the same. To a contrary, the imaging conditions may be different from each other irrespective of contributing to the water excitation or not so that each of the imaging conditions is to be proper.

Figure 6:
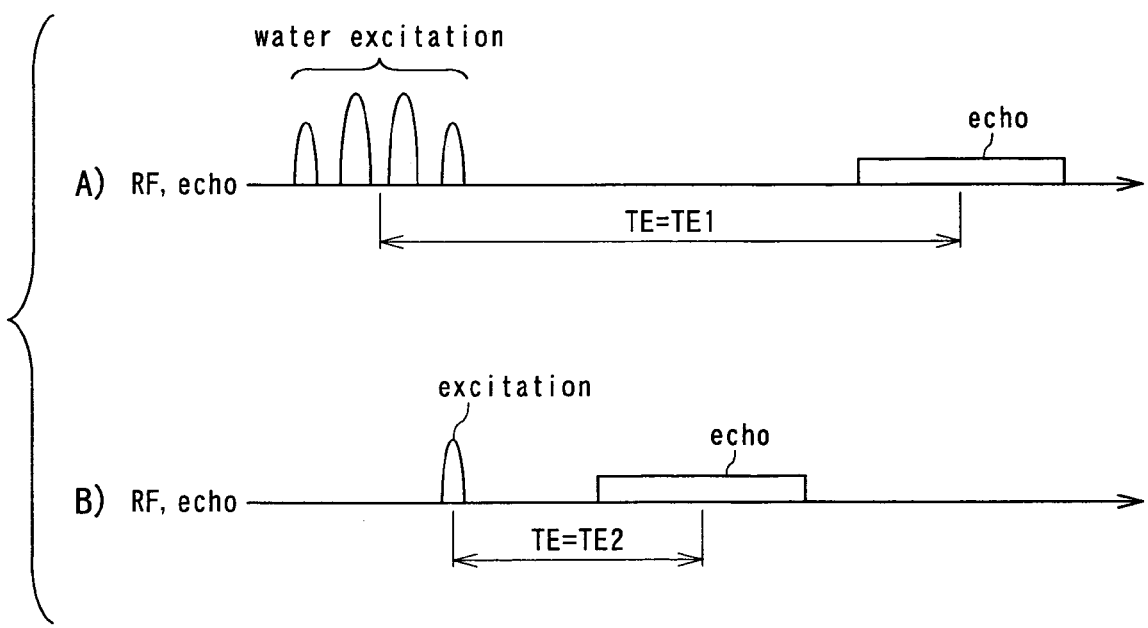
FIG. 6 is a diagram showing an example of a sequence used in a case where a scan is performed with switching the existence of the fat-water separation with a water-excitation method while fundamental imaging conditions are not to be identity in the magnetic resonance imaging apparatus shown in FIG. 1.

FIG. 6 is a diagram showing an example of a sequence used in a case where a scan is performed with switching the existence of the fat-water separation with a water-excitation method while fundamental imaging conditions are not to be identity in the magnetic resonance imaging apparatus 20 shown in FIG. 1.

Referring to FIG. 6, a sequence for acquiring the MR signal with the water excitation is generated for imaging the slices overall the head of the object P. Another sequence for acquiring the MR signal with exciting both the water and the fat is generated for imaging the slices including the replacement area of the three dimensional image data. More specifically, the sequence with the water excitation for imaging the overall the head is set so as to apply a water excitation pulse group having a plurality of excitation pulses for water excitation as shown A) of FIG. 6. An echo time TE1 until acquiring the MR signal is set to be relatively long.

The sequence without the water excitation is set to have a general excitation pulse for exciting both the water and the fat as shown B) of FIG. 6. The sequence without the water excitation is also set so as to acquire the MR signal with an echo time TE2 shorter than the echo time TE1 of the sequence with the water excitation as shown in A) of FIG. 6

If the scanning operation is executed with the sequence shown in B) of FIG. 6, even in the case of the scanning operation of the curve portion 51, e.g., near the carotid syphone 50A, the reduction in a signal value of the blood flow due to the turbulence of blood flow at the curve portion 51 is suppressed with the property resistant against the uneven static magnetic field. Thus, the property for extracting the blood flow is improved.

As mentioned above, an imaging condition, such as the echo time, without contributing to the fat-water separation can be properly set. Further, in the case of the fat saturation method, imaging conditions other than the fat saturation pulse may be varied depending on a condition, such as an imaging object.

In addition, whole sequences for imaging the entire head are generated by combining the sequence with the fat-water separation and the sequence without the fat-water separation. The whole sequences for imaging the entire head are formed by arbitrarily aligning the sequences for the slices as shown FIGS. 5 and 6. Preferably, the whole sequences are generated so as to reduce an imaging interval of the slice common to the scanning operation with the fat-water separation and the scanning operation without the fat-water separation.

Figures 7, 8:
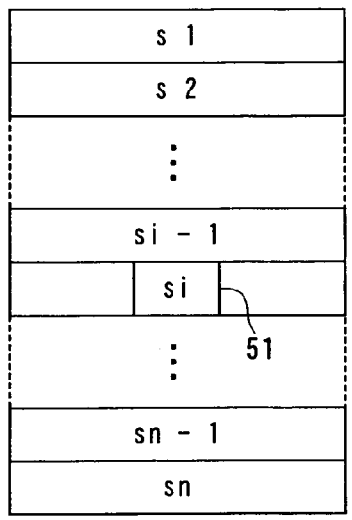
FIG. 7 is a diagram showing an example of slabs which is to be imaging objects by the magnetic resonance imaging apparatus shown in FIG. 1.
FIG. 8 is a diagram showing an imaging order for the slabs shown in FIG. 7 and the existence of the fat-water separation.

FIG. 7 is a diagram showing an example of slabs which is to be imaging objects by the magnetic resonance imaging apparatus 20 shown in FIG. 1. FIG. 8 is a diagram showing an imaging order for the slabs shown in FIG. 7 and the existence of the fat-water separation.

According to a preferable embodiment, a sequential multi-slab method (also referred to as an MOSTA method) is used for imaging operation while sequentially changing three dimensional slab for imaging target.

Referring to FIG. 7, when an i-th slab si of n slabs (s1, s2, . . . , sn) includes the curve portion 51 set as the replacement area of the three dimensional image data, the sequence is generated so as to go on the scanning operation of all n slabs (s1, s2, . . . , sn) with the fat-water separation in the order of the body axis Z.

Further, the i-th slab si is subjected to the scanning operation without the fat-water separation, in addition to the scanning operation with the fat-water separation. The timing of scanning operation of the i-th slab si without the fat-water separation is set before/after another arbitrary scanning operation. Preferably, the scanning operation of the i-th slab si without the fat-water separation is executed before/after the scanning operation of the i-th slab si with the fat-water separation.

In the case of executing the scanning operation of the i-th slab si without the fat-water separation after the scanning operation of the i-th slab si with the fat-water separation, the scanning operations are executed in the order shown in FIG. 8.

As mentioned above, the order of scanning operations is set. Thus, the imaging interval of the common slab is reduced and the influence from the motion of the object P can be suppressed.

In the case of a plurality of slabs including the curve portion 51, similarly, the scanning operations of the slabs without the fat-water separation can be executed before/after the corresponding scanning operations of the slabs with the fat-water separation respectively. Alternatively, the scanning operations may be executed so that the imaging intervals are reduced as much as possible by switching the existence of the fat-water separation by a plurality of slabs.

Then, the imaging condition setting unit 44 gives the generated sequence to the sequence controller control unit 40.

In step S3, the scanning operation is executed by switching the existence of the fat-water separation in accordance with the imaging condition set by the imaging condition setting unit 44. The three dimensional image data as a result of the scanning operation with the fat-water separation and the three dimensional image data without the fat-water separation are reconstructed respectively.

That is, the object P is set to the bed 37, and a static magnetic field is generated at an imaging area of the magnet 21 (a superconducting magnet) for static magnetic field excited by the static-magnetic-field power supply 26. Further, the shim-coil power supply 28 supplies current to the shim coil 22, thereby uniformizing the static magnetic field generated at the imaging area.

The input device 33 sends an operating command to the sequence controller control unit 40. The sequence controller control unit 40 supplies the sequence received from the imaging condition setting unit 44 to the sequence controller 31, thereby controlling the driving operation of the sequence controller 31. Therefore, the sequence controller 31 drives the gradient power supply 27, the transmitter 29, and the receiver 30 in accordance with the sequence received from the sequence controller control unit 40, thereby generating, at the imaging area having the set object P, an X-axis gradient magnetic field Gx, a Y-axis gradient magnetic field Gy, and a Z-axis gradient magnetic field Gz and further generating RF signals.

In this case, the X-axis gradient magnetic field Gx, Y-axis gradient magnetic field Gy, and Z-axis gradient magnetic field Gz generated by the gradient coils are mainly used as an gradient magnetic field for phase encode (PE), an gradient magnetic field for read out (RO), and an gradient magnetic field for slice (SL), respectively. Consequently, the regularity exists in the rotating directions of nucleus spins within the object P. The gradient magnetic fields for PE and RO individually convert the X coordinate and the Y coordinate into the quantity of phase variety and the quantity of frequency variety of the nucleus spins within the object P. The X coordinate and the Y coordinate are two-dimensional positional information on the slices formed in the Z-axis direction serving as the body axis by the gradient magnetic field for SL.

The transmitter 29 sequentially supplies the RF signals to the RF coil 24 in accordance with the sequence, and the RF coil 24 transmits the RF signals to the object P.

The sequence set by the imaging condition setting unit 44 is set for the purpose of obtaining an MRA image of blood flow at a portion, such as the head. Therefore, the MR signal from the fat is suppressed so as to sufficiently obtain the contrast between the blood flow region and a parenchymal portion other than the blood flow region. Further, all the slabs overall the imaging area are subjected to the fat-water separation exciting the MR signal from the water which is a component of the blood flow.

The fat-water separation method includes the pre-pulse method and the water excitation method as shown in FIGS. 5 and 6. For example, the pre-pulse method is used and the fat saturation pulse is applied to the object P as a pre-pulse, prior to acquire the MR signal which is used as the original data for generating the blood flow image. Therefore, when the imaging area includes the entire head, prior to acquire the data on slabs of the entire head, the fat saturation pulse selectively excites protons in the fat depending on the frequency, thereby setting the protons to a saturating state.

The protons in the fat enter the saturating state and then the acquisition of data on the MR signal for generating a blood flow image starts. That is, an excitation pulse, serving as a RF signal, is transmitted to the object P, the RF coil 24 receives the MR signals generated by the nuclear magnetic resonance of nucleuses within the object P, and the received signals are sequentially given to the receiver 30. Since the protons in the fat are in the saturating state, the MR signal from the fat is suppressed.

As mentioned above, the fat is saturated, thereby improving the contrast between the blood flow region and the parenchymal region other than the blood flow region. The static magnetic field is uneven at the curve portion 51, e.g., near the carotid syphone 50A, and thus the fat is not preferably saturated. The MR signal from the water which is a component of the blood flow may be lost.

Thus, from the slab including the curve portion 51, e.g., near the carotid syphone 50A, the data on the MR signal with the fat saturation pulse and that without the fat saturation pulse are acquired in accordance with the sequence set by the imaging condition setting unit 44. For example, the data on the MR signal without the fat saturation pulse are acquired subsequently to the acquisition of data on the MR signal with the fat saturation pulse. The interval for acquiring the data on the MR signal from the same slab can be further reduced. Therefore, the amount of positional shift due to the motion of the object P can be reduced.

The RF coil 24 receives the MR signals from the slabs. Then, the receiver 30 receives the MR signals from the RF coil 24 and executes various signal processing including the pre-amplification, conversion of intermediate frequency, phase detection, amplification of low frequency, and filtering, to the received MR signals. Further, the receiver 30 converts an analog MR signal into a digital signal, thereby generating the raw data, serving as the MR signal in the form of the digital data. The receiver 30 supplies the generated raw data to the sequence controller 31.

The sequence controller 31 supplies the raw data received from the receiver 30 to the sequence controller control unit 40. The sequence controller control unit 40 arranges the raw data to the k space generated in the raw data database 42. The raw data database 42 stores the raw data of the slabs of the object P.

Further, the image reconstructing unit 41 captures the raw data from the raw data database 42 and performs predetermined image reconstructing processing, such as three dimensional Fourier transform, thereby reconstructing the three dimensional image data of the object P and writing the data to the image data database 43. As a result, the image data database 43 stores the three dimensional image data of the entire head obtained with the fat-water separation and the three dimensional image data of the slab including the curve portion 51, e.g., near the carotid syphone 50A, obtained without the fat-water separation.

In step S4, the image data editing unit 46 reads both the three dimensional image data obtained with the fat-water separation and the three dimensional image data obtained without the fat-water separation from the image data database 43, and the portion of the replacement area received from the combination area setting unit 45, of the three dimensional image data imaged with the fat-water separation, is replaced with the three dimensional image data imaged without the fat-water separation, thereby additionally generating the three dimensional image data.

The sequential multi-slice method is described above as an example in the assumption that one slab si includes the carotid syphone 50A. When a plurality of slabs, e.g., a slab si and a slab si+1 include the carotid syphone 50A, it is possible to obtain both data with the fat-water separation and those without the fat-water separation according to each of the two slabs. Further, in the imaging operation of "sliding MR imaging" for imaging while sliding the slabs, it is possible to obtain both data with the fat-water separation and those without the fat-water separation according to a part of the slabs. In this case, preferably, the data with the fat-water separation and those without the fat-water separation are subjected to the sliding three dimensional reconstruction respectively.

As mentioned above, the three dimensional image data partly including two types of data is obtained. Hereinbelow, since the concept of slab on acquisition is not necessary, the word of "slice" is used for expression.

Figure 9:
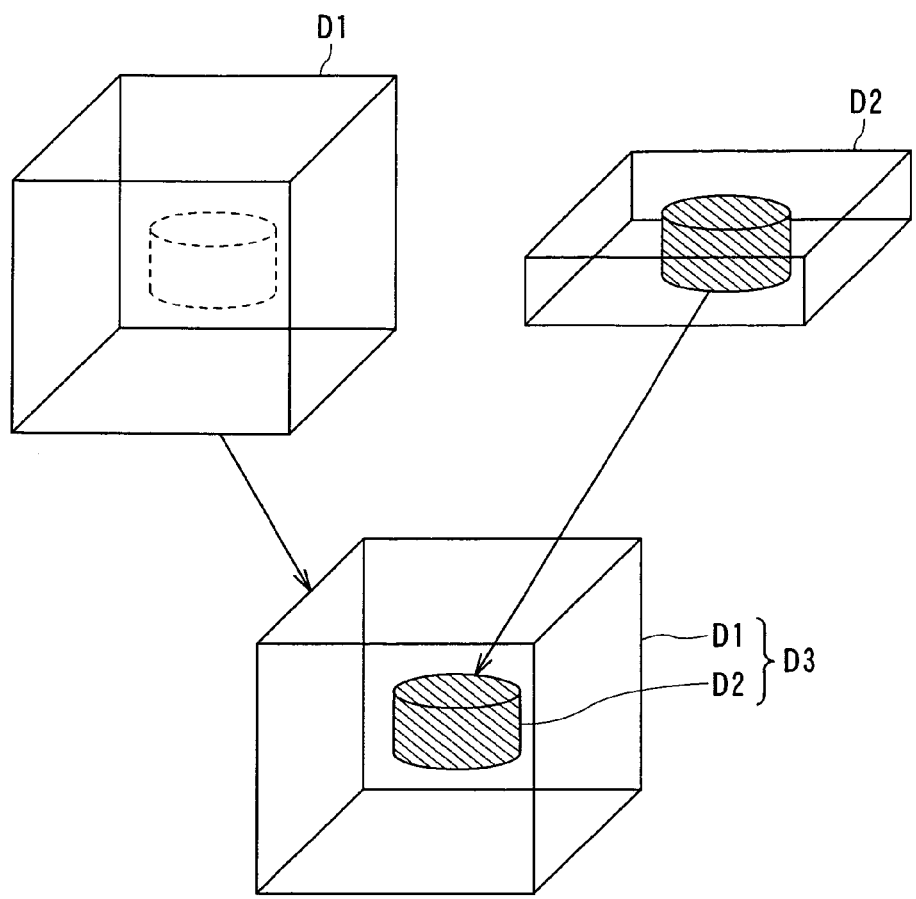
FIG. 9 is a diagram explaining a method for replacing three dimensional image data in the magnetic resonance imaging apparatus shown in FIG. 1.

FIG. 9 is a diagram explaining a method for replacing three dimensional image data in the magnetic resonance imaging apparatus 20 shown in FIG. 1.

Referring to FIG. 9, the image data editing unit 46 reads three dimensional image data D1 of the entire head obtained with the fat-water separation and three dimensional image data D2 of the slice including the curve portion 51, obtained without the fat-water separation, from the image data database 43. Here, the replacement area is set by the combination area setting unit 45 and, upon generating the MRA image of the entire head, the replacement area corresponds to the curve portion 51, e.g., near the carotid syphone 50A.

The image data editing unit 46 replaces the replacement area shown with dotted lines of the three dimensional image data D1, corresponding to the entire head, imaged with the fat-water separation by the replacement area (shaded portion) of the three dimensional image data D2 corresponding to the slice imaged without the fat-water separation, thereby additionally generating three dimensional image data D3.

As a consequence, the three dimensional image data D3 is generated. The three dimensional image data D3 has the three dimensional image data D2 obtained without the fat-water separation at the curve portion 51 having a danger that the MR signal from the blood flow is lost due to an insufficient fat-water separation. On the other hand, the three dimensional image data D3 has the three dimensional image data D1 obtained with the fat-water separation at the portion other than the curve portion 51, in which it is needed to saturate fat, in order to extract a blood vessel. The portion other than the curve portion 51 includes the portion near a scalp.

However, if a part of the three dimensional image data D1 with the fat-water separation is simply replaced by the three dimensional image data D2 without the fat-water separation, the border of the replacement area (shaded portion) in the newly-generated three dimensional image data D3 may not be smoothed.

Then, the image data editing unit 46 weights the three dimensional image data D1 imaged with the fat-water separation and the three dimensional image data D2 without the fat-water separation if necessary and combines the weighted three dimensional image data D1 and the weighted three dimensional image data D2, thereby smoothing the newly-generated three dimensional image data D3.

Figure 10:
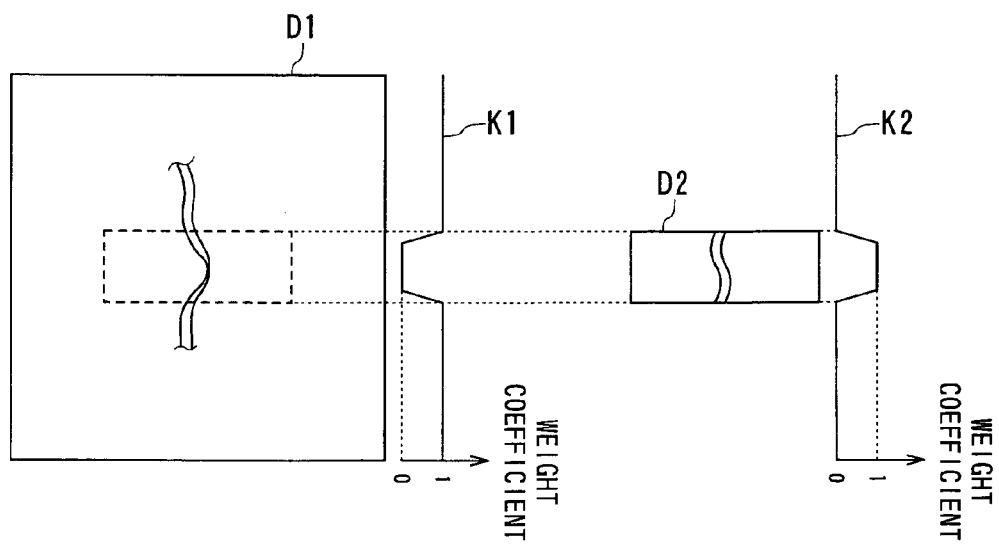
FIG. 10 is a diagram explaining an example of weighting processing performed when single three dimensional image data is generated respectively from the three dimensional image data obtained respectively with switching the existence of the fat-water separation in the magnetic resonance imaging apparatus shown in FIG. 1.

FIG. 10 is a diagram explaining an example of weighting processing performed when single three dimensional image data is generated from the three dimensional image data obtained respectively with switching the existence of the fat-water separation in the magnetic resonance imaging apparatus 20 shown in FIG. 1.

Referring to FIG. 10, the reference symbol D1 denotes the three dimensional image data on the entire head, imaged with the fat-water separation. As shown by the three dimensional image data D1 in FIG. 10, the defect of the fat-water separation suppresses the image of the blood vessel at the replacement area within a dotted line having the uneven magnetic field. On the other hand, the reference symbol D2 denotes the three dimensional image data to be combined to the replacement area of the three dimensional image data D1 in FIG. 10. The three dimensional image data D2 is of the replacement area, imaged without the fat-water separation. As shown by the three dimensional image data D2 in FIG. 10, imaging the replacement area without the fat-water separation allows the image of a blood vessel to be represented satisfactory although the replacement area has the uneven magnetic field.

In order to replace the replacement area of the three dimensional image data D1 shown in FIG. 10 with the three dimensional image data D2, the pixel values of the data D1 and D2 are added each other. However, the simple addition may not smooth the image of the border of the replacement area.

Then, in the addition of the three dimensional image data D1 and D2, weight coefficients according to the distance from the border of the replacement area are used for weighting addition. The weight coefficients are shown in graphs on the left to the three dimensional image data D1 and D2 in FIG. 10 respectively. The axes in the graphs in FIG. 10 denote values of the weight coefficients which range from 0 to 1, as a standard value respectively.

That is, the weight coefficient K1 for the three dimensional image data D1 of the replacement area having the suppressed an image of blood vessels is 1 out of the replacement area. As farther from the border of the replacement area, the weight coefficient K1 gradually reduces and finally becomes 0. The weight coefficient K2 for the three dimensional image data D2 of the replacement area having an image of blood vessels which is preferably drawn is 0 out of the replacement area. As farther from the border of the replacement area, the weight coefficient K2 gradually increases and finally becomes 1. Then, the three dimensional image data D1 and D2 are weighted and added by using the above-set weight coefficients K1 and K2. Thus, the image of blood vessels can preferably be drawn with the smoothness near the border of the replacement area irrespective of the region with even magnetic field.

The image data editing unit 46 gives the generated three dimensional image data to the projection image generating unit 48 and the edited image referring unit 47.

In step S5, the edited image referring unit 47 generates an image data for referring for checking whether or not the replacement area is properly set and the MRA image is preferably generated by using the three dimensional image data received from the image data editing unit 46 as the original data. The image data for referring by which the user can check whether or not the range or position of the replacement area is proper has an arbitrary format or range. The image data for referring can be arbitrary image data, such as SVR image data, as well as MIP image data. For example, the edited image referring unit 47 generates the MIP image data only near the replacement area, as the image data for referring, by using the MIP processing, gives the generated MIP image data to the monitor 34.

Therefore, the monitor 34 displays the MIP image near the replacement area, and the user can determines whether or not the replacement area is properly set, e.g., whether or not the range or position of the replacement area is shifted. When the replacement area is not properly set, in step S6, an instruction for resetting the replacement area is inputted from the input device 33. Then, in step S1, the replacement area starts to be set again.

When the replacement area is properly set and an instruction for resetting the replacement area is not inputted from the input device 33, in step S7, the MIP image data from the three dimensional image data is generated, and is displayed, as an MRA image, on the monitor 34. That is, the projection image generating unit 48 performs the MIP processing of the three dimensional image data received from the image data editing unit 46, thereby generating the MIP image data. Further, the generated MIP image data is given to the monitor 34. Therefore, the monitor 34 displays the MIP image of the blood vessel preferably-drawn as the MRA image irrespective of the region with the even magnetic field. That is, at the curve portion 51, e.g., near the carotid syphone 50A, the MRA image without the fat-water separation is set. On the other hand, at another region having the even magnetic field, the MRA image with the advantage of the fat-water separation is set.

When the edited image referring unit 47 generates the MIP image data of the entire head for check operation to be displayed, another MIP image data does not need to be generated. In this case, the edited image referring unit 47 has the shared function of the projection image generating unit 48.

That is, in the imaging operation of the MRA image, the above-mentioned magnetic resonance imaging apparatus 20 has a function for obtaining both the images with and without the fat-water separation at the area where the fat-water separation is not to be sufficient, replacing the three dimensional image data obtained with the fat-water separation to the three dimensional image data partially having data without the fat-water separation, and performing the MIP processing to the replaced data.

Therefore, even at the curve portion 51, such as the syphone portion of the head, at which the fat is not conventionally saturated sufficiently, the magnetic resonance imaging apparatus 20 selectively performs the fat-water separation of only the portion with the preferable fat-water separation without the complicated imaging processing, such as Partial MIP. Thus, the magnetic resonance imaging apparatus 20 obtains the wide MRA image with preferable contrast. That is, although the penalty is imposed, e.g., the scanning time is slightly prolonged, the MR signal from the fat component is suppressed and the MRA image without the loss of MR signal from the blood flow is obtained.

Figure 11:
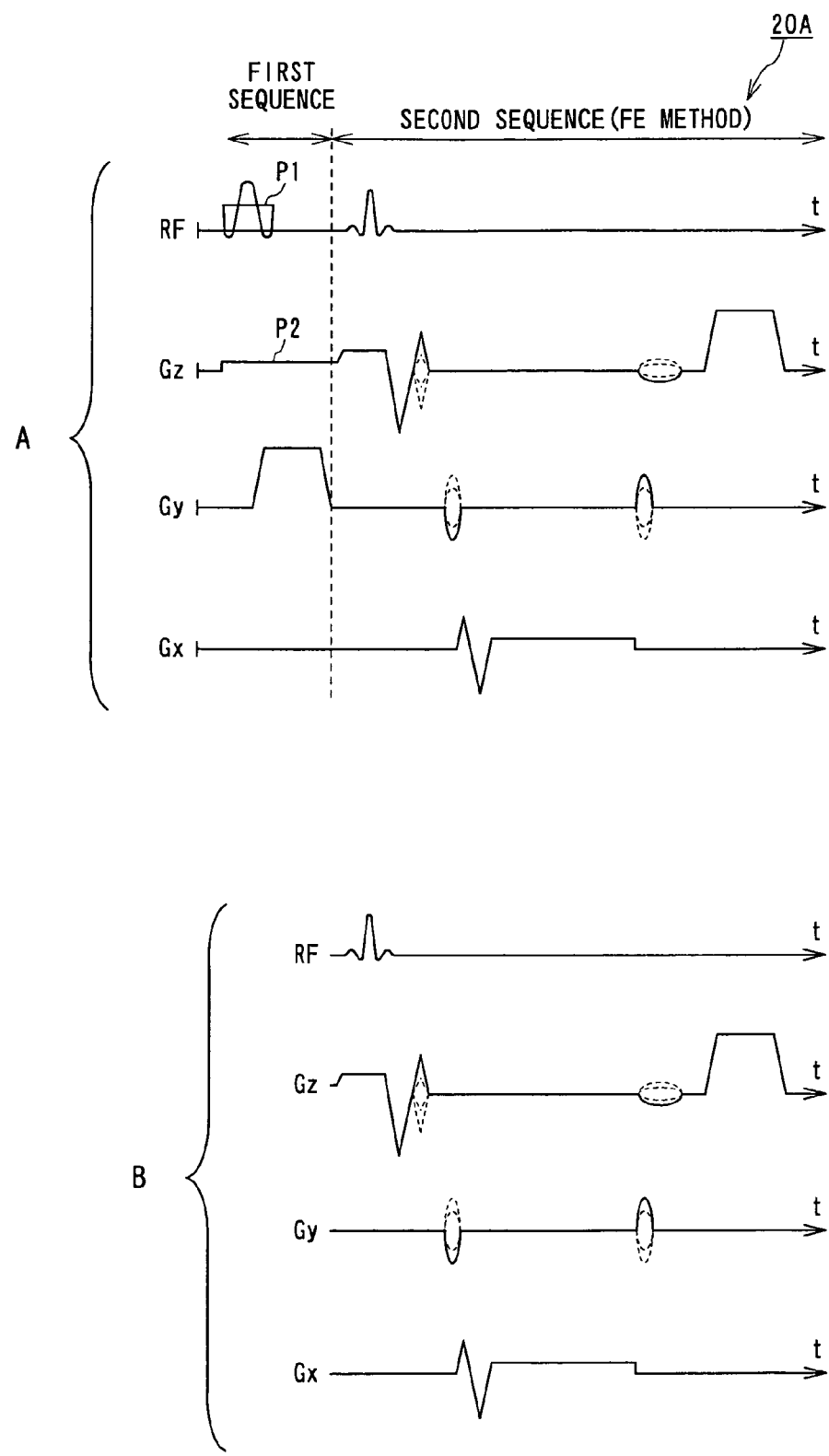
FIG. 11 is a diagram showing an example of a sequence for describing a magnetic resonance imaging apparatus according to a second embodiment of the present invention.

FIG. 11 is a diagram showing an example of a sequence for describing a magnetic resonance imaging apparatus according to a second embodiment of the present invention.

In the magnetic resonance imaging apparatus 20A according to a second embodiment shown in FIG. 11, a sequence generated by the imaging condition setting unit 44 and the fact that the fat-water separation does not used are different from those of the magnetic resonance imaging apparatus 20 shown in FIG. 1. Other constructions and operations of the magnetic resonance imaging apparatus 20A are not different from those of the magnetic resonance imaging apparatus 20 shown in FIG. 1 substantially. Therefore, only an example of sequence structure is shown, omitting explanation regarding a same component and operation of the magnetic resonance imaging apparatus 20A.

The magnetic resonance imaging apparatus 20A uses the MT advantage, as an improving method for the contrast of an MRA image, in place of the fat-water separation. Referring to A) of FIG. 11, a first sequence is set so that an MTC pulse P1 is applied to the object P, as a pre-pulse, prior to the data acquisition of the blood flow image. Then, subsequent to the first sequence, for example, a second sequence for acquiring the image data on field echo (FE) method is set.

Accurately, the first sequence shown in A) of FIG. 11 uses an SORS (slice-selective off-resonance sinc pulse) pulse for applying a slice gradient pulse P2 for selective excitation of the MTC excitation surface at substantially the same timing as the MTC pulse P1.

Figure 12:
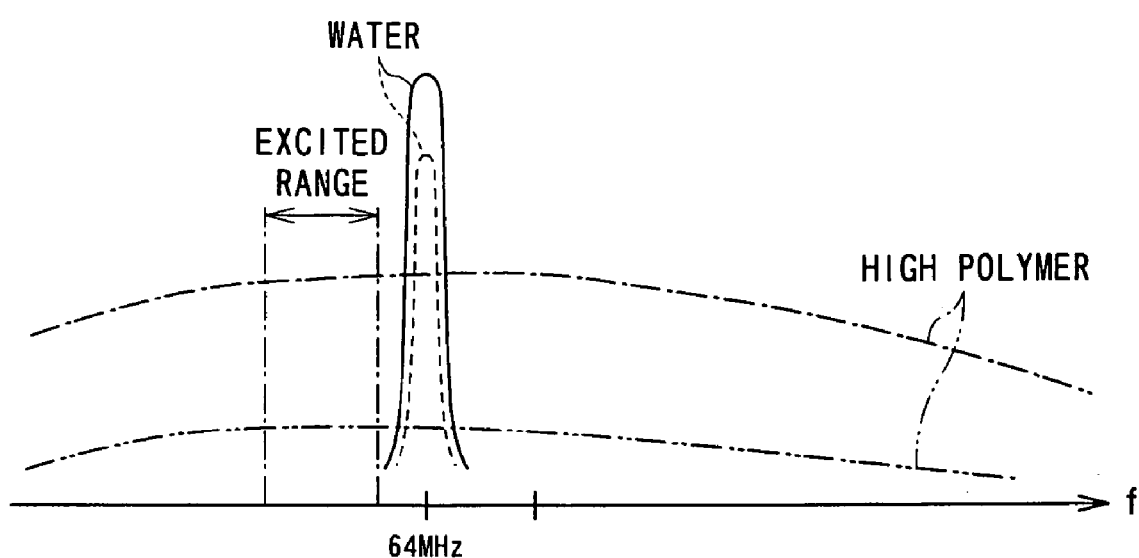
FIG. 12 is a diagram which compares the spectrum of the proton contained in water and that in a high polymer for explaining a MT effect obtained due to a MTC pulse on the sequence shown as A) in FIG. 11.

FIG. 12 is a diagram which compares the spectrum of the proton contained in water and that in a high polymer for explaining a MT effect obtained due to a MTC pulse on the sequence shown as A) in FIG. 11.

In FIG. 17, the solid line shows the spectrum of the proton contained in water, and the chain line shows that in a high polymer. If a frequency shifted from 64 MHz, serving as the resonant frequency of the proton of water, by 500 Hz is selectively excited by an RF pulse, such an MT advantage is obtained that the MR signal level from the proton of the high polymer and the MR signal level from the proton of water are reduced respectively.

In FIG. 12 the dashed line shows a spectrum of the proton contained in water after a MR signal level of the proton falls due to the MT effect. The chain double-dashed line shows the spectrum of the proton contained in a high polymer after a MR signal level of the proton falls due to the MT effect.

The use of the above-mentioned MT advantage enables the imaging operation of images including an MRA image with the contrast according to the rate of high polymer (fat).

Referring to FIG. 12, with the MT advantage, such a feature is known that the MR signal level at the fat region having the high polymer component is excessively reduced, as compared with the MR signal level at the blood flow region having the water component. In order to obtain the MT advantage, the SORS pulse is generated as the first sequence so that the MTC pulse P1 is applied to the object P as the pre-pulse.

The scanning operation with applying the MTC pulse P1 enables the imaging operation of the MRA image with the contrast according to the MT advantage. In particular, advantageously, the MRA image with the extraction of the thin blood vessel is obtained.

To the contrary, depending on the fat rate, preferably, the MRA image or the like with the original contrast without the MT advantage is obtained as image for diagnosis. However, when mixedly existing the region at which it is preferable to apply the MTC pulse P1 to obtain the MT advantage and the region at which it is preferable to acquire the MR signal without the MT advantage, one of the two imaging conditions is used.

In this case, the region at which it is not preferable to apply the MTC pulse P1 is set as the replacement area. The slice including the replacement area is subjected to both of the scanning operation with applying the MTC pulse P1 and the scanning operation without applying the MTC pulse P1. The entire imaging area is subjected to the execution of scanning operation with applying the MTC pulse P1. That is, the imaging condition setting unit 44 generates the sequence without applying the MTC pulse P1 for scanning the slice including the replacement area, as shown in B) of FIG. 11. The sequences shown in A) and B) of FIG. 11 are selectively used every slice, and the scanning operation is executed.

The replacement area of the three dimensional image data obtained by the scanning operation with applying the MTC pulse P1 is replaced with the three dimensional image data obtained by the scanning operation without applying the MTC pulse P1. Thus, it is possible to obtain the image, such as the MRA image, using the MT advantage for only the proper area.

Depending on the imaging condition, the entire imaging area is scanned without applying the MTC pulse P1. On the other hand, the slice including the replacement area is subjected to the execution of both the scanning operation with applying the MTC pulse P1 and the scanning operation without applying the MTC pulse P1. The replacement area of the three dimensional image data obtained by the scanning operation without applying the MTC pulse P1 may be replaced with the three dimensional image data obtained with applying the MTC pulse P1.

That is, the magnetic resonance imaging apparatus 20A according to the second embodiment is a device switching the existence of applying the MTC pulse P1, in place of switching the existence of the fat-water separation, serving as a different point of the imaging conditions in the magnetic resonance imaging apparatus 20 shown in FIG. 1 according to the first embodiment.

As mentioned above, the difference of the imaging conditions at the replacement area is typically caused by the existence of the fat-water separation or applying the MTC pulse P1. Such imaging conditions can be variously set. For example, the imaging conditions are set to be different each other by combining the fat-water separation and the applying operation of the MTC pulse P1, thereby executing the scanning operation of the replacement area on the set imaging conditions.

Further, the scanning operation may be executed under three or more different imaging conditions, and the three dimensional image data obtained under two or more arbitrary imaging conditions may be combined. For example, a number n of imaging conditions is set, including an imaging condition with the fat-water separation, an imaging condition without the fat-water separation, an imaging condition without applying the MTC pulse, and an imaging condition with applying the MTC pulse. Then, three dimensional image data obtained with applying the MTC pulse and without applying the MTC pulse and three dimensional image data obtained by switching the existence of the fat-water separation are individually combined, thereby obtaining the image with various contrasts.

In the magnetic resonance imaging apparatuses 20 and 20A according to the first and second embodiments, the three dimensional image data obtained under one imaging condition is partially replaced with the three dimensional image data obtained under another imaging condition. For example, when all the slices are imaged under varied imaging conditions respectively, in addition to the replacement, the three dimensional image data of the slices obtained under the imaging condition respectively may be simply combined, thereby generating new three dimensional image data.

What is claimed is:

1. A magnetic resonance imaging apparatus comprising:
   an imaging condition setting unit configured to set a first contrast imaging condition and a second contrast imaging condition;
   a gradient coil configured to impress gradient magnetic fields to an object in a static magnetic field in accordance with the first imaging condition and the second imaging condition;
   a radio frequency coil configured to transmit radio frequency signals to the object in accordance with the first imaging condition and the second imaging condition;
   a data acquisition unit configured to acquire first magnetic resonance signal data corresponding to the first imaging condition and second magnetic resonance signal data corresponding to the second imaging condition from the object;
   an image reconstructing unit configured to reconstruct first three dimensional image data regarding the object in accordance with the first magnetic resonance signal data and second three dimensional image data regarding the object in accordance with the second magnetic resonance signal data; and
   an image data generating unit configured to combine the first three dimensional image data and the second three dimensional image data to generate third three dimensional image data.

2. A magnetic resonance imaging apparatus according to claim 1,
   further comprising a projection image generating unit configured to generate maximum intensity projection image data by performing a maximum intensity projection processing to the third three dimensional image data.

3. A magnetic resonance imaging apparatus according to claim 1,
   wherein the imaging condition setting unit is configured to set an imaging condition with a fat-water separation serving as the first imaging condition and an imaging condition without the fat-water separation serving as the second imaging condition.

4. A magnetic resonance imaging apparatus according to claim 1,
   wherein the imaging condition setting unit is configured to set an imaging condition with impressing a magnetization transfer contrast pulse serving as the first imaging condition and an imaging condition without impressing the magnetization transfer contrast pulse serving as the second imaging condition.

5. A magnetic resonance imaging apparatus according to claim 1,
   wherein the image data generating unit is configured to generate the third three dimensional image data by replacing a part of one of the first three dimensional image data and the second three dimensional image data to a corresponding part of an other.

6. A magnetic resonance imaging apparatus according to claim 1,
   wherein the image data generating unit is configured to generate the third three dimensional image data by replacing a part of a slice on one of the first three dimensional image data and the second three dimensional image data to a corresponding part of a corresponding slice on an other.

7. A magnetic resonance imaging apparatus according to claim 1,
   further comprising a combination area setting unit configured to generate arbitrary image data as reference image data to give a monitor to make a reference image displayed on the monitor and set a combination area in accordance with an information for designating an area received from an input device, the combination area being used for the image data generating unit configured to generate the third three dimensional image data.

8. A magnetic resonance imaging apparatus according to claim 1,
   further comprising an image referring unit configured to subject the third three dimensional image data to an image processing to generate image data used for reference and give the image data used for reference which is generated to a monitor to make an image used for reference displayed on the monitor.

9. A magnetic resonance imaging apparatus according to claim 1,
   wherein the imaging condition setting unit is configured to set the first imaging condition with a fat-water separation and the second imaging condition without the fat-water separation, a first sub-imaging-condition without contribution for the fat-water separation included in the first imaging condition and a second sub-imaging-condition corresponding to the first sub-imaging-condition in the second imaging condition being equivalent each other.

10. A magnetic resonance imaging apparatus according to claim 1,
    wherein the imaging condition setting unit is configured to set the first imaging condition with a fat-water separation and the second imaging condition without the fat-water separation, a first sub-imaging-condition without contribution for the fat-water separation included in the first imaging condition and a second sub-imaging-condition corresponding to the first sub-imaging-condition in the second imaging condition being appropriate conditions which are different each other.

11. A magnetic resonance imaging apparatus according to claim 1,
wherein the image data generating unit is configured to generate the third three dimensional image data by adding the first three dimensional image data and the second three dimensional image data each other with weights to replace a part of one of the first three dimensional image data and the second three dimensional image data to a corresponding part of an other, the third three dimensional image data having a replacement area of which a boundary part is smooth.

12. A magnetic resonance imaging apparatus according to claim 1,
wherein the image data generating unit is configured to generate the third three dimensional image data by replacing a part of a slice on one of the first three dimensional image data and the second three dimensional image data to a corresponding part of a corresponding slice on an other, and
the imaging condition setting unit is configured to set the first imaging condition and the second imaging condition to have an reduced acquisition interval between first specific magnetic resonance signal data obtained from a specific slice with the first imaging condition and second specific magnetic resonance signal data obtained from the specific slice with the second imaging condition.

13. A magnetic resonance imaging apparatus comprising:
means for setting a first contrast imaging condition and a second contrast imaging condition;
means for impressing gradient magnetic fields to an object in a static magnetic field in accordance with the first imaging condition and the second imaging condition;
means for transmitting radio frequency signals to the object in accordance with the first imaging condition and the second imaging condition;
means for acquiring first magnetic resonance signal data corresponding to the first imaging condition and second magnetic resonance signal data corresponding to the second imaging condition from the object;
means for reconstructing first three dimensional image data regarding the object in accordance with the first magnetic resonance signal data and second three dimensional image data regarding the object in accordance with the second magnetic resonance signal data; and
means for combining the first three dimensional image data and the second three dimensional image data to generate third three dimensional image data.

14. A magnetic resonance imaging method comprising steps of:
setting a first contrast imaging condition and a second contrast imaging condition;
impressing gradient magnetic fields to an object in a static magnetic field in accordance with the first imaging condition and the second imaging condition;
transmitting radio frequency signals to the object in accordance with the first imaging condition and the second imaging condition;
acquiring first magnetic resonance signal data corresponding to the first imaging condition and second magnetic resonance signal data corresponding to the second imaging condition from the object;
reconstructing first three dimensional image data regarding the object in accordance with the first magnetic resonance signal data and second three dimensional image data regarding the object in accordance with the second magnetic resonance signal data; and
combining the first three dimensional image data and the second three dimensional image data to generate third three dimensional image data.

15. A magnetic resonance imaging method according to claim 14,
further comprising a step of generating maximum intensity projection image data by performing a maximum intensity projection processing to the third three dimensional image data.

16. A magnetic resonance imaging method according to claim 14,
wherein an imaging condition with a fat-water separation is set as the first imaging condition and an imaging condition without the fat-water separation is set as the second imaging condition.

17. A magnetic resonance imaging method according to claim 14,
wherein an imaging condition with impressing a magnetization transfer contrast pulse is set as the first imaging condition and an imaging condition without impressing the magnetization transfer contrast pulse is set as the second imaging condition.

18. A magnetic resonance imaging method according to claim 14,
wherein the third three dimensional image data are generated by replacing a part of one of the first three dimensional image data and the second three dimensional image data to a corresponding part of an other.

19. A magnetic resonance imaging method according to claim 14,
wherein the third three dimensional image data are generated by replacing a part of a slice on one of the first three dimensional image data and the second three dimensional image data to a corresponding part of a corresponding slice on an other.

20. A magnetic resonance imaging method according to claim 14,
further comprising steps of generating arbitrary image data as reference image data to give a monitor to make a reference image displayed on the monitor; and
setting a combination area in accordance with an information for designating an area received from an input device, the combination area being used for generating the third three dimensional image data.

21. A magnetic resonance imaging method according to claim 14,
further comprising steps of subjecting the third three dimensional image data to an image processing to generate image data used for reference; and
giving the image data used for reference which is generated to a monitor to make an image used for reference displayed on the monitor.

22. A magnetic resonance imaging method according to claim 14,
wherein the first imaging condition with a fat-water separation and the second imaging condition without the fat-water separation are set, a first sub-imaging-condition without contribution for the fat-water separation in the first imaging condition and a second sub-imaging-condition corresponding to the first sub-imaging-condition in the second imaging condition being equivalent each other.

23. A magnetic resonance imaging method according to claim 14,
wherein a first imaging condition with a fat-water separation and a second imaging condition without the fat-water separation are set, a first sub-imaging-condition without contribution for the fat-water separation in the first imaging condition and a second sub-imaging-condition corresponding to the first sub-imaging-condition in the second imaging condition being appropriate conditions which are different each other.

24. A magnetic resonance imaging method according to claim 14,
wherein the third three dimensional image data are generated by adding the first three dimensional image data and the second three dimensional image data each other with weights to replace a part of one of the first three dimensional image data and the second three dimensional image data to a corresponding part of an other, the third three dimensional image data having a replacement area of which a boundary part is smooth.

25. A magnetic resonance imaging method according to claim 14,
wherein the third three dimensional image data are generated by replacing a part of a slice on one of the first three dimensional image data and the second three dimensional image data to a corresponding part of a corresponding slice on an other, and
the first imaging condition and the second imaging condition Is set to have an reduced acquisition interval between first specific magnetic resonance signal data obtained from a specific slice with the first imaging condition and second specific magnetic resonance signal data obtained from the specific slice with the second imaging condition.

* * * * *